US008696655B2

United States Patent
Dolleris et al.

(10) Patent No.: US 8,696,655 B2
(45) Date of Patent: Apr. 15, 2014

(54) SELF-CONTAINED HANDPIECE AND METHOD FOR OPTICAL TISSUE SURFACE TREATMENT

(75) Inventors: Casper Dolleris, Vancouver (CA); Claus Dolleris, Skibby (DK)

(73) Assignee: Intenzity Innovation APS, Hvidovre (DK)

( * ) Notice: Subject to any disclaimer, the term of this patent is extended or adjusted under 35 U.S.C. 154(b) by 501 days.

(21) Appl. No.: 12/595,495

(22) PCT Filed: Apr. 10, 2008

(86) PCT No.: PCT/US2008/059932
§ 371 (c)(1),
(2), (4) Date: Mar. 25, 2010

(87) PCT Pub. No.: WO2008/124839
PCT Pub. Date: Oct. 16, 2008

(65) Prior Publication Data
US 2011/0137303 A1    Jun. 9, 2011

Related U.S. Application Data

(60) Provisional application No. 60/911,021, filed on Apr. 10, 2007.

(51) Int. Cl.
*A61B 18/18* (2006.01)
*A61B 19/00* (2006.01)

(52) U.S. Cl.
USPC .................... 606/17; 606/2; 606/9; 128/898

(58) Field of Classification Search
USPC .......................... 606/2–19; 128/898
See application file for complete search history.

(56) References Cited

U.S. PATENT DOCUMENTS

| 5,432,622 A | 7/1995 | Johnston et al. |
| 5,620,478 A | 4/1997 | Eckhouse ............. 607/88 |

(Continued)

FOREIGN PATENT DOCUMENTS

| JP | 2003-79752 | 3/2003 |
| WO | 2005/099369 | 10/2005 |

OTHER PUBLICATIONS

Extended European Search Report dated Nov. 5, 2010, for EP Patent Application No. 08 745 530.9.

(Continued)

*Primary Examiner* — Dawayne A Pinkney
(74) *Attorney, Agent, or Firm* — Vista IP Law Group, LLP

(57) ABSTRACT

A handpiece for treatment of the surface of a target tissue with at least one light beam is provided, the handpiece including a housing, at least one light source for generating at least one light beam, an opening for allowing the emission of the at least one light beam out of the housing and towards the target surface, a mechanism for controlled displacement of the at least one light source to move the at least one light beam across the target surface; and a controller for controlling the mechanism. A method is provided for treating a tissue surface with a light beam that includes directing a light beam towards the tissue surface, focusing the light beam at the tissue surface so that the focal point is positioned proximate the surface of the tissue so that the diameter of the light beam is smaller at the surface of the tissue than below the surface. The light beam is moved to create a pattern on the tissue, and it is moved in response to manual movement of the handpiece to overcome unwanted movements and provide a desired spot pattern on the tissue surface.

76 Claims, 11 Drawing Sheets

Light source and optics is contained in handheld unit as well as a controller and user interface.

(56) References Cited

U.S. PATENT DOCUMENTS

| | | | |
|---|---|---|---|
| 5,971,978 A * | 10/1999 | Mukai | 606/18 |
| 2002/0161357 A1 | 10/2002 | Andeson et al. | |
| 2003/0216719 A1 | 11/2003 | DeBenedictis et al. | |
| 2004/0147984 A1 | 7/2004 | Altshuler et al. | |
| 2005/0154380 A1 | 7/2005 | DeBenedictis et al. | |
| 2005/0154381 A1 * | 7/2005 | Altshuler et al. | 606/9 |
| 2006/0116669 A1 | 6/2006 | Dolleris | |
| 2006/0217787 A1 | 9/2006 | Olson et al. | |
| 2008/0077198 A1 * | 3/2008 | Webb et al. | 607/88 |

OTHER PUBLICATIONS

International Preliminary Report and Written Opinion dated Sep. 17, 2008, for PCT Patent Application No. PCT/US2008/059932.

European Office Action dated Apr. 23, 2012, for EP Patent Application No. 08 745 530.9.

\* cited by examiner

Light source and optics is contained in handheld unit as well as a controller and user interface.

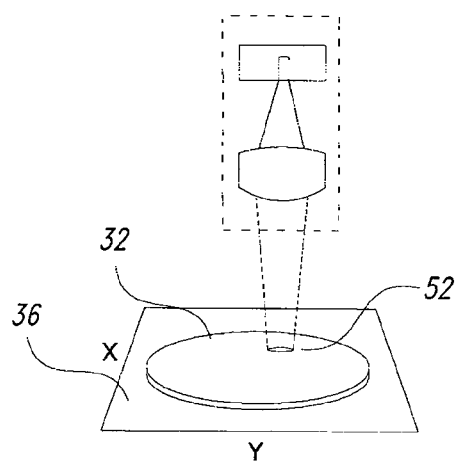
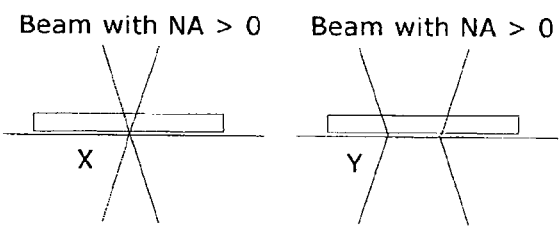
FIG. 5A
FIG. 5B    FIG. 5C
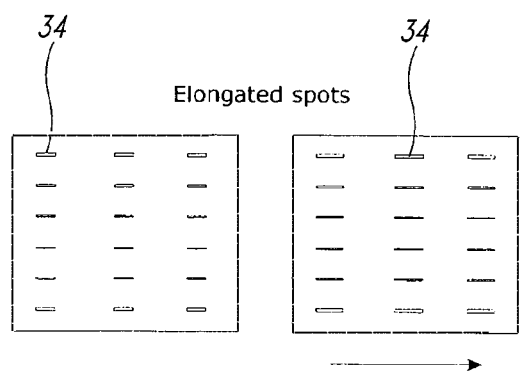
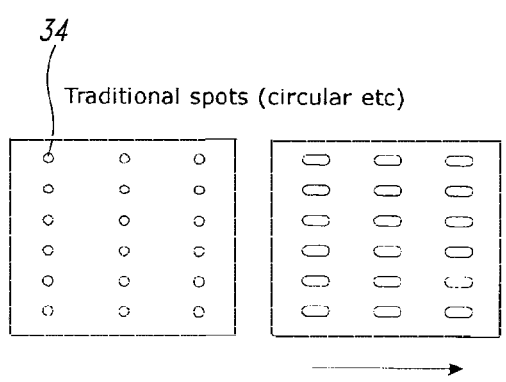
FIG. 6A — No movement during treatment
FIG. 6B — Movement during treatment causes only slight area increase
FIG. 6C — No movement during treatment
FIG. 6D — Device is moving during treatment and causes significant area increase

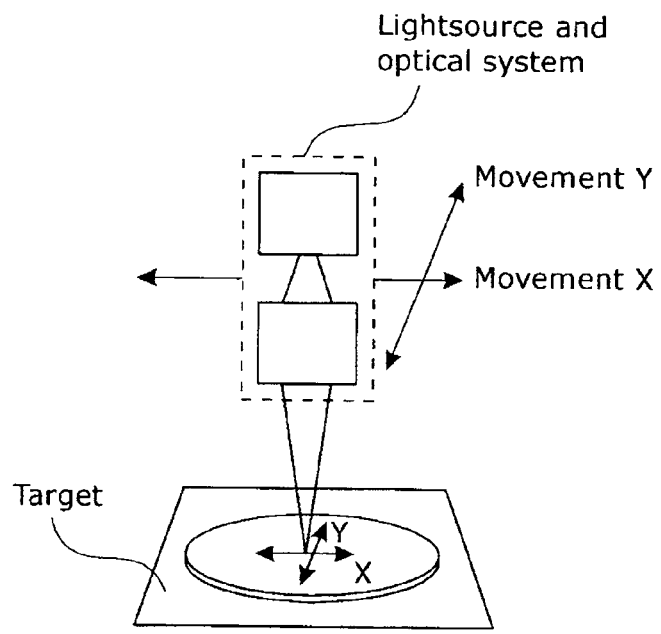
FIG. 9
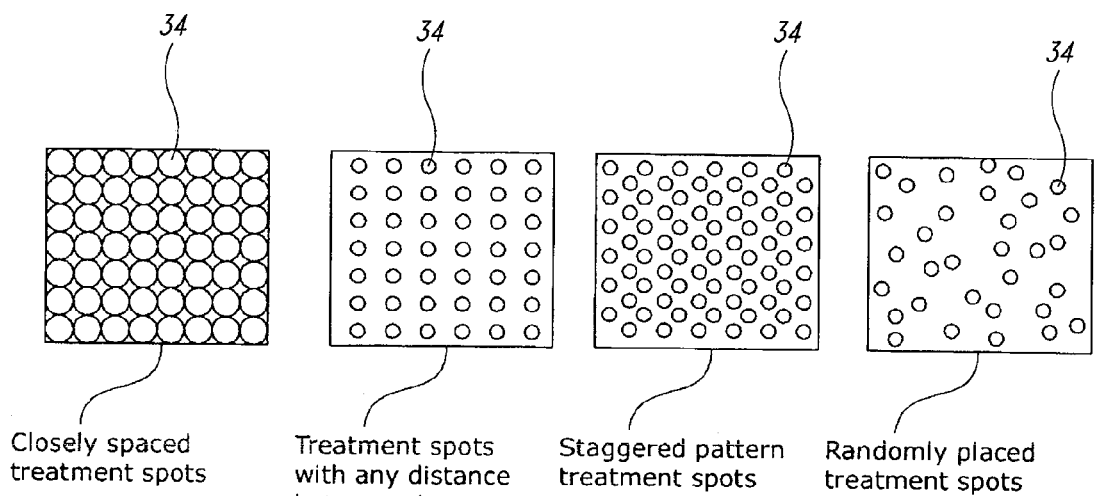
Closely spaced treatment spots
FIG. 10A
Treatment spots with any distance between them
FIG. 10B
Staggered pattern treatment spots
FIG. 10C
Randomly placed treatment spots
FIG. 10D

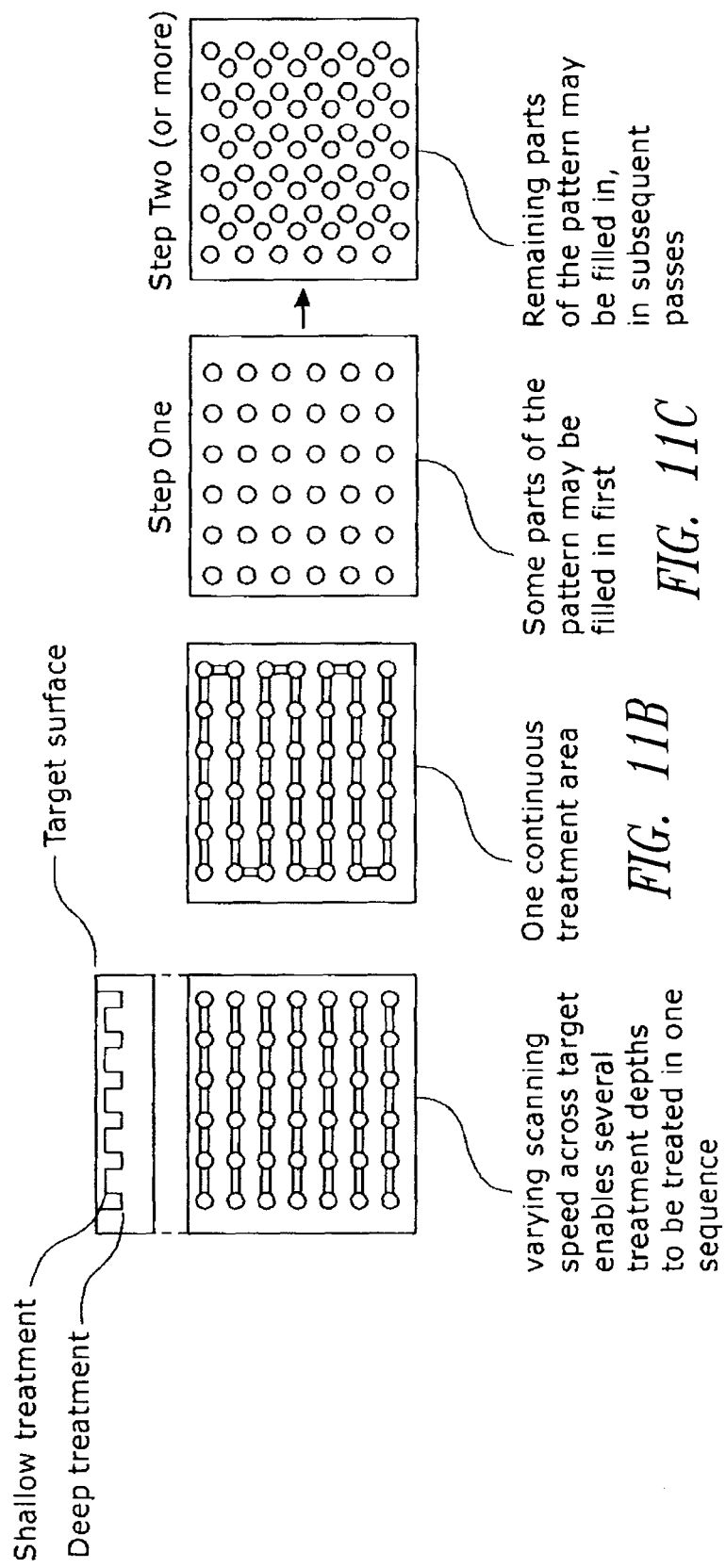

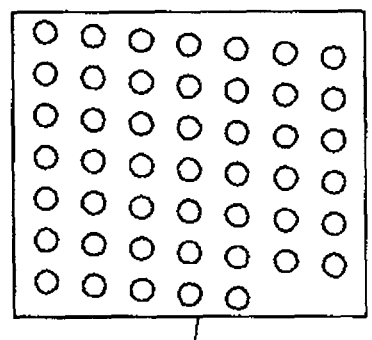
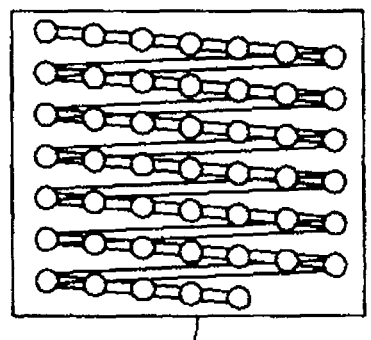
Pattern from one-dimensional scanning and handpiece movement
Single continuous treatment pattern from one-dimensional scanning
*FIG. 12A*  *FIG. 12B*

Simple implementation of optical system with a single aspheric lens and a laser diode.

In this example two light sources are being used giving two discrete target spots at the same time.

SELF-CONTAINED HANDPIECE AND METHOD FOR OPTICAL TISSUE SURFACE TREATMENT

RELATED APPLICATION DATA

The application is the national stage of PCT Application No. PCT/US08/059,932, filed on Apr. 10, 2008, now expired, which claims priority to and the benefit of U.S. Provisional Patent Application No. 60/911,021, filed on Apr. 10, 2007, the disclosures of both of these applications are expressly incorporated by reference in their entirety herein.

BACKGROUND OF THE INVENTION

1. Field of the Invention

The present disclosure relates to an apparatus for treatment of a tissue surface with light and more particularly to a handpiece with a light source and related method of treatment.

2. Description of the Related Art

Handpieces for use in treating tissue with light are well known. These handpieces represent a substantial investment, and there is a need for a self-contained handpiece that is not only economical but is versatile and adaptable to home use by those not skilled in the medical arts.

BRIEF SUMMARY OF THE INVENTION

The present disclosure is directed to a handpiece for treatment of tissue surface with a light beam that is moved across at least a portion of the target area. The handpiece includes a housing accommodating at least one light source for generating at least one light beam, an opening or output port for passage of the at least one light beam towards the tissue surface, a moving mechanism for controlled displacement of the at least one light source for moving the at least one light beam across the tissue surface, and a controller for controlling the moving mechanism.

The handpiece may further include an optical system for focusing the at least one light beam.

In a preferred embodiment, the tissue surface is the surface of human skin.

Further, a method is provided for treating a tissue surface with a light beam that includes the steps of directing a light beam towards the tissue surface, focusing the light beam at the tissue surface so that the focal point is positioned proximate the surface of the tissue so that the diameter of the light beam is smaller at the surface of the tissue than below the surface.

For example, a method is provided for treating human skin by using a light beam with a wavelength of between 400 nm and 4000 nm and a power density sufficiently high for creating a temporary channel into the skin, resulting in increased transparency through the skin and thereby facilitating treatment of deeper tissue structures.

Further, a method is provided for treating human skin with a light beam that includes the step of focusing the light beam on treatment spots on the skin, the treatment spots having an area at the skin surface sufficiently small to cause the treatment spots not to be visible to the naked eye at a viewing distance of 30 cm or more.

Still further, a method is provided for treating human skin with a light beam emitted from a handpiece, the light beam illuminating a spot on the surface of the target tissue, the light beam having an elongated shape, the method including the step of moving the handpiece in the direction of elongation whereby the spot area increase due to handpiece movement is minimized.

A method is also provided for treating human skin with a light beam, including the step of irradiating the surface of the skin with a spot having an area smaller than 0.1 mm$^2$ to allow the irradiated surface area to heal very quickly.

A method is further provided for treating human skin with a light beam that includes the step of focusing the light beam in such a way that the area of a spot illuminated on the tissue surface is less than 0.5 mm$^2$, such as less than 0.4 mm$^2$, or less than 0.3 mm$^2$, or less than 0.2 mm$^2$, or less than 0.1 mm$^2$, and the area receives a power density sufficiently high for creating a channel into the skin thereby enhancing the effect of a substance applied to the surface of the tissue in the target area.

The enhanced effect may, for example, be created by increased penetration of the substance into the skin because of the apertures or channels created by the irradiation. The substance may be applied to the skin surface before or after the optical treatment of the skin surface.

BRIEF DESCRIPTION OF THE SEVERAL VIEWS OF THE DRAWINGS

The foregoing and other features and advantages of the present disclosure will be more readily appreciated as the same becomes better understood from the following detailed description of exemplary embodiments when taken in conjunction with the accompanying drawings, wherein:

FIGS. 5A-5C schematically illustrate an elongated spot and different focal patterns;

FIGS. 6A-6D schematically illustrate a tissue surface treatment with elongated spots versus traditional spots;

FIG. 9 schematically illustrates a fourth embodiment of the present disclosure;

FIGS. 10A-10D schematically illustrate first treatment patterns generated with an embodiment of the present disclosure;

FIGS. 11A-11D schematically illustrate second treatment patterns generated with an embodiment of the present disclosure;

FIGS. 12A-12B schematically illustrate third treatment patterns generated with an embodiment of the present disclosure;

The foregoing figures are schematics and are simplified for clarity. They merely show details that are essential to the understanding of the disclosure, while other details have been left out. Throughout, the same reference numerals are used for identical or corresponding parts.

DETAILED DESCRIPTION OF PREFERRED EMBODIMENTS

The embodiments of the present disclosure will now be described more fully hereinafter with reference to the accompanying drawings, in which exemplary embodiments of the invention are shown. The disclosure may, however, be embodied in different forms and should not be construed as limited to the embodiments set forth herein. Rather, these embodiments are provided so that this disclosure will be thorough and complete and will more fully convey the concept of the invention to those skilled in the art.

Figure 1:
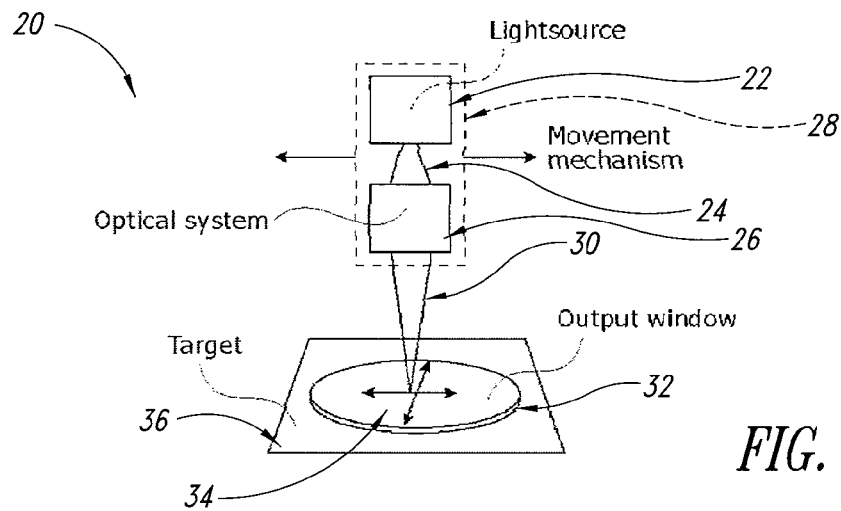
FIG. 1 schematically illustrates a first embodiment of the present disclosure.
Figure 2A:
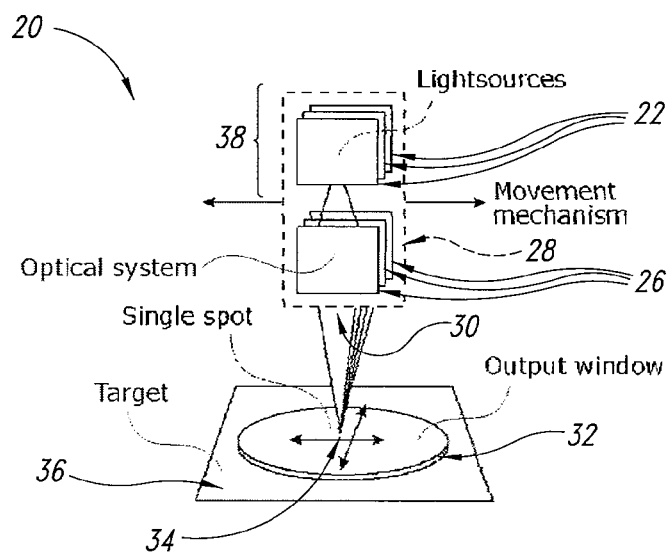
FIGS. 2A-2B schematically illustrate a second embodiment of the present disclosure.
Figure 2B:
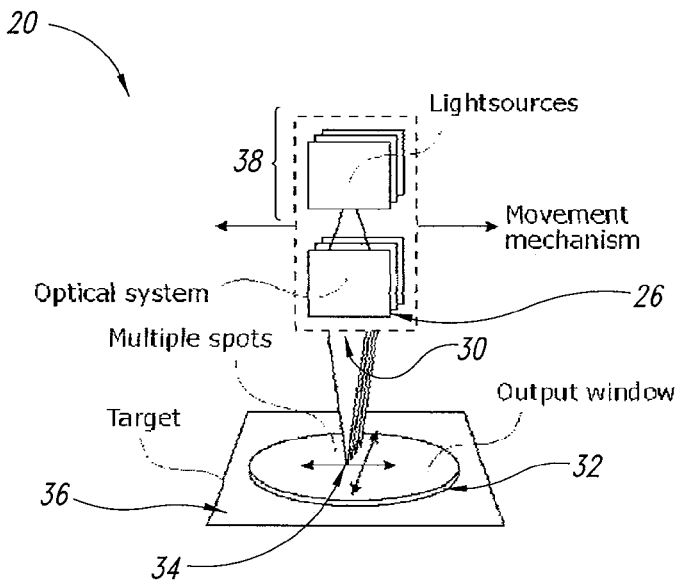

Referring initially to FIGS. 1 and 2A-2B, shown therein is a simplified schematic of a handheld surface tissue treatment device 20 having a light source 22 generating light 24 through an optical system 26, which undergo selective movement by a movement mechanism 28. Emitted light beam 30 exits an output window 32 with a focal point 34 on a target tissue 36.

The light source 22 may be constituted by a single light source, a plurality of separate light sources, or an array of light sources. The light source 22 can emit light 24 of wavelengths different from the wavelengths emitted by other light sources of a set 38 of light sources. Further, a light source in a set 38 of light sources can emit light 24 with an output power different from the output power emitted by other light sources of the set 38 of light sources. Output beams 30 emitted by a plurality of light sources in a set 38 of light sources can be configured to coincide to generate a single beam of light, as shown in FIG. 2A, having a light spectrum that is a combination of the light spectrum emitted by the plurality of light sources 22, which can each have their own optical system 26 or utilize a single optical system. Utilization of a plurality of light sources can decrease treatment duration. On the other hand, each light source in the set 38 of light sources can be maintained as a separate light beam 30 by the optical system 26.

In the illustrated embodiments, the moving mechanism 28 is adapted for displacement of both the set 38 of light sources 22 and the optical system 26. Alternatively, only the optical system 26 can be moved, although this is suboptimal for a variety of reasons.

A cooling element (not shown) may actively or passively cool the set of light sources. Cooling elements such as heat-pipes, heat sinks, water, thermo-electric coolers, fans, etc., or any combination thereof can be used.

When in operation, the light source 22 illuminates the target surface 36 with one or more focused light beams 34. These light beams 34 are mechanically directed in their location by the moving mechanism 28, and in one embodiment the moving mechanism 28 sweeps the light beam 30 or set of light beams 30 across the target surface 36. Alternatively, the light beams 30 may be positioned in predetermined or random positions in relation to the target surface 36 as a function of time. Alternatively, the light source 22 can be pulsed to obtain individual treatment spots on the target surface, or the set of light sources 38 may emit light continuously to obtain continuous traces across the target surface 36. These continuous traces may abut or overlap to obtain a continuous area of treated tissue, for example, for skin rejuvenation.

Depending on the parameters of the light 24 generated from the light source 22, such as wavelength, intensity, fluence, power density, pulse width, pulse duty cycle, etc., tissue at the treatment spot(s) 34 may respond in various ways. For example, the tissue may be ablated, forming an ablated area on the tissue surface 36. Tissue may also be heated without ablation, and it may be heated for protein denaturation. A photo-acoustic thermal effect can be created that ruptures the tissue, and spots of photo-biological stimulation may be formed.

Figure 3:
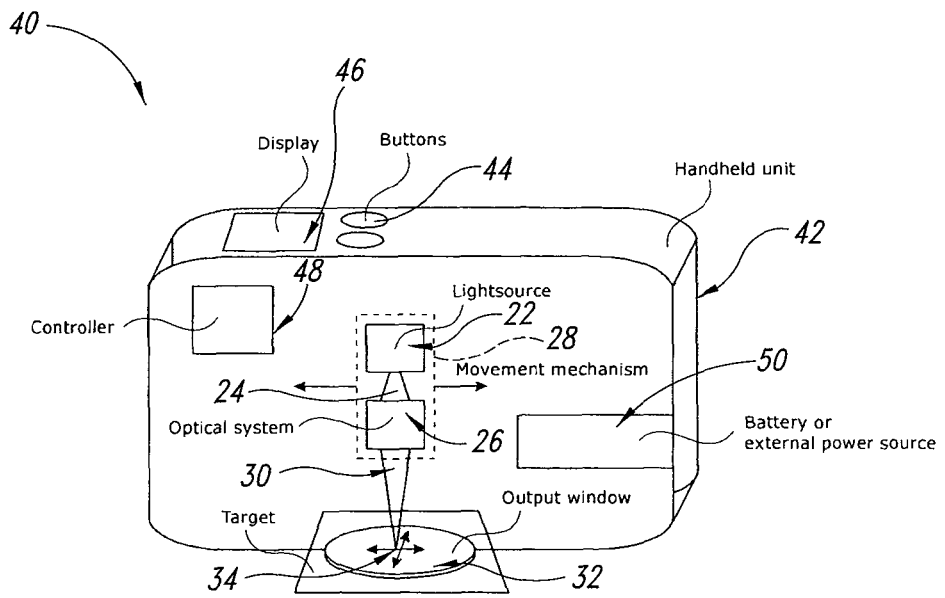
FIG. 3 schematically illustrates a third embodiment of the present disclosure.

Referring next to FIG. 3, shown therein in schematic form is a handpiece 40 having mounted therein the light source 22, optical system 26, movement mechanism 28, and output window 32 through which the emitted light beam 30 is focused. The handpiece 40 generally includes a body 42 sized and shaped for manual holding with one hand by an operator. The body includes buttons 44 on an accessible surface for manipulation by the user to control the light source 22 and movement mechanism 28. A display 46 provides feedback to the user. The buttons 44 are coupled to a controller 48 that in turn is coupled to the light source 22 and movement mechanism 28. Power is supplied by either an internal battery 50 or external power source.

The controller 48 is adapted to control the moving mechanism 28 and the light source 22 or set of light sources 38 for illumination of a one, two, or three-dimensional pattern on the target surface. For example, the treatment pattern on the target surface 36 may comprise individual spots 34, linear traces, or nonlinear traces to form areas of treated tissue and untreated tissue. The treatment pattern on the target surface 36 may comprise continuous areas of treated tissue, for example continuous areas that are obtained by abutting or overlapping linear or nonlinear traces with the light beam 30.

As is evident from the foregoing, the handpiece 40 may be manually moved to direct the light beam 30 to selected target tissue 36, or the moving mechanism 28 can be used to move the light beam 30 while the handpiece 40 is held stationary against the treated tissue 36. In this regard, the moving mechanism 28 can displace the light source 22 and optical system 26 with one degree of freedom for moving the light beam 30 across a corresponding set of linear or nonlinear traces on the target surface 36. In combination with this movement generated by the moving mechanism 28, the handpiece 40 can be moved continually or continuously to achieve a two-dimensional exposure of the tissue surface 36.

In an alternative embodiment, the moving mechanism 28 can displace the light beam 30 with two degrees of freedom, moving the light beam 30 across a corresponding set of linear or nonlinear traces on the target surface 36 multiple times to position sets of traces adjacent to each other or in overlapping or abutting relationship. In combination with the foregoing, the handpiece 40 may be moved in steps to cover a tissue area of any selected size.

The embodiment illustrated in FIG. 3 shows the output port 32 in the form of a window that is transparent to the set of light beams. In one embodiment, the window 32 is made of glass and preferably coated to minimize reflections. During operation of the handpiece 40, the window 32 is positioned on and pressed against the tissue surface 36 so that the tissue surface abuts an outer surface of the window 32. In this way, the optical distance between the optical system 26 and the target surface 36 is maintained at a constant distance, which is known.

Preferably, the light beam 30 or set of light beams 30 is preferably focused at the outer extreme of the tissue surface, which would be the outer surface of the window 32 so that, during treatment, the light beam 30 is focused at the surface of the tissue, thereby confining tissue treatment to the surface without damaging tissue below the surface.

The window 32 can become heated with transmission of the light beam 30 therethrough. If necessary, the window can be cooled using a fan, a peltier element, water, or other known cooling methods.

The light source 22 is in a preferred embodiment a laser diode, or a high power light emitting diode, a solid-state laser, or other source of similar size that can be moved by the moving mechanism 28 in the handpiece 40. Laser diodes are preferred because they are compact, efficient, and have excellent optical characteristics that, in combination with a high-quality optical system 26, can provide a number of advantageous beam profiles for treatment of the target surface 36. In order to obtain a therapeutic effect for skin treatment, a certain fluence level is required, as disclosed in more detail herein. In the handpiece 40 of the present disclosure, the required fluence level can be achieved with a relatively low power light source because of the direct focusing method of the optical system that leads to illumination of small-sized spots on the target surface.

Figure 4:
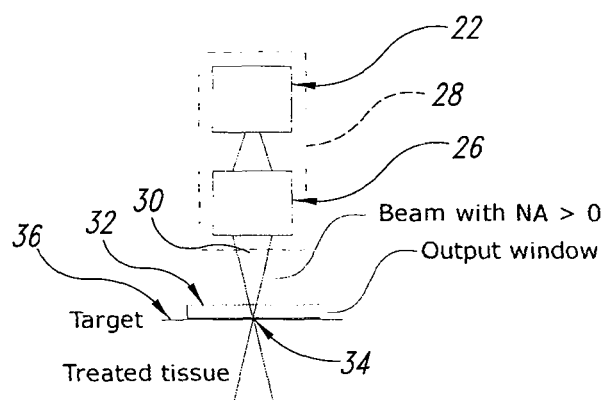
FIG. 4 schematically illustrates a highly focused light beam.

More particularly, an important advantage of the handpiece 40 according to the present disclosure is the movement of the light source 22 by the moving mechanism 28 to make it possible to optimize the optical system 26 to provide a focused light beam 30 or set of light beams 30 illuminating very small spots on the target surface 36. For example, each spot may have an area of less than 10,000 $\mu m^2$. Alternatively, the spot can have an area of less than 8,000 $\mu m^2$, 6,000 $\mu m^2$, and preferably less than 5,000 $\mu m^2$. Thus, each spot may receive light with a high power density and fluence. This is illustrated in FIG. 4, in which the light spot 34 is highly focused by the optical system 26 on the surface of the target tissue 36, which can create an entry point in the form of ablated or non-ablated microchannel through the upper skin layer.

The power density may be larger than 10 $kW/cm^2$, or larger than 20 $kW/cm^2$, and even larger than 30 and 40 $kW/cm^2$. In addition, the fluence may be larger than 50 $J/cm^2$, such as 100 $J/cm^2$, 150 $J/cm^2$, and even larger than 200 $J/cm^2$.

The ability of the handpiece 40 according to the present disclosure to illuminate very small spots with a high fluence opens up new realms of tissue surface treatment. For example, when the light beam 30 is concentrated and the fluence and power density is very high, the light beam 30 can ablate tissue at the tissue surface and thereby create a small aperture or channel at the focus point 34 on the tissue surface 36. Because the light beam 30 diverges at a very large angle when it propagates into the tissue, the fluence and power density decreases rapidly as a function of tissue depth so that only the uppermost part of the tissue surface is ablated. Due to its small size, the aperture or channel in the tissue heals very quickly, such as within minutes.

The handpiece 40 described herein so far will be safe to operate in a home environment or elsewhere. Further, should the light beam become defocused, the power density will be too low to damage any tissue.

The temporary aperture or channel formed in the treated tissue will allow the light beam 30 to pass without attenuation and dispersion for improved light treatment of tissue immediately below the aperture. According to one aspect of the present disclosure, a method is provided for treating human skin with a light beam having sufficient high power density, for example above 20 $kW/cm^2$, and preferably in the range of 5-20 $kW/cm^2$, for temporarily creating an aperture or a channel in the skin surface and thereby allowing treatment of deeper tissue structures. The required power density will depend on the wavelength of the emitted light. For example, a higher power density will be required for a wavelength of 980 nm where tissue absorption is lower than will be required for a wavelength, such as 1450 nm, where tissue absorption is high.

Furthermore, the temporary apertures or channels may lead to increased penetration through the tissue of a treating substance applied to the area to be treated before or after the optical treatment, thereby improving the treatment effect of the applied substance.

Referring next to FIGS. 5A-5C, the light beam 30 is focused on an elongated treatment spot 52 on the surface 36 of the tissue to create a "knife edge" incision into the tissue surface with minimum damage to the upper tissue layers. The focused elongated treatment spot 52 creates an elongated aperture or a channel in the tissue having an opening area that can be extremely small while simultaneously exposing a larger deeper tissue area due to the large angle of divergence of the beam 30 propagating into the tissue. The size of the deeper treated tissue area will depend on the angle of divergence of the light beam 30.

The elongated light beam 30 may be emitted by a laser diode 22 that has a very small beam width (typically 1 $\mu m$) and an elongated beam (typically 1:100 or 1:1000) along the other axis perpendicular to the small width. A high fluence, typically above 200 $J/cm^2$ to 1000 $J/cm^2$, and potentially much higher, can be achieved by direct exposure using a highly focused laser diode.

FIGS. 6A-6D illustrate different treatment patterns. For example, tissue can be treated with an elongated light beam and the handpiece moved manually in the direction of the elongation as shown in FIGS. 6A and 6B. The movement will not cause substantial area enlargement of the treatment spots 34. For example, in FIGS. 6C and 6D, a circular beam is used to generate a circular spot 34 that will result in a substantially larger area if the handpiece is not kept in a fixed position relative to the target area, as shown in FIG. 6D.

For example, if a circular spot with 100 $\mu m$ diameter is used, and the movement during the spot exposure is 0.3 mm, the resulting spot area will increase by roughly 300%. In contrast, if an elongated spot of 10 $\mu m$ by 500 $\mu m$ is used, the area increase will only be 60%. This is a substantial difference when it is required to keep the spot size as small as possible.

In one embodiment of the disclosure, the fluence required for a specific treatment is delivered to the illuminated spots with constant spot size, power and energy settings during the treatment. To maintain small spot sizes, it is important that the optical distance between the optical system and the target surface is constant so that the positions of the focus points of the set of light beams do not change in relation to the target surface. This may for example be obtained by provision of the previously mentioned window at the output port or by having a spacer with a thin slit that allows light through while maintaining the distance to the skin.

Varying the spot size may be advantageous for some tissue treatment methods. The spot size may be varied dynamically by changing parameters of the optical system or by varying the distance between the optical system and the target.

In the illustrated embodiments, the moving mechanism preferably moves the set of light sources in a plane parallel to the target surface and thus keeps the distance from the optical system to the target surface constant during light source displacement.

The high degree of light beam focusing provided by preferred embodiments of the disclosure leads to illumination of very small spots on the target surface, which again leads to coverage of a small percentage of the target surface within a certain time period. In order to avoid excessive duration of a treatment, the moving mechanism must displace the set of light beams quickly. This again requires that the set of light sources, and possibly also the optical system, have a very low mass.

In one embodiment, the light beam may be pulsed with pulses of 10 ms duration of a 1 W light beam resulting in emission of 10 mJ. It is preferred that the moving mechanism is capable of completing a movement between emitted pulses. A low moving mass of a few grams, such as 10 grams and a powerful voice coil system will allow the movement duration to be a few milliseconds. In other embodiments the treatment energy could be from less than 1 mJ to many joules and the laser power could be less than 1 mW to hundreds of watts depending on the specific application to facilitate fast treatment or low impact treatments.

The movement mechanism may be realized in a number of ways, for example as a voice coil system with position feedback (preferred), a mechanical rotating moving mechanism, a galvanometer, a screw and slide system, etc.

A voice coil system may comprise a coil mounted on the moving assembly, magnets on one or two sides of the coil, and a position feedback system that may be magnetic (preferred), optic, capacitive, etc.

Figure 7A:
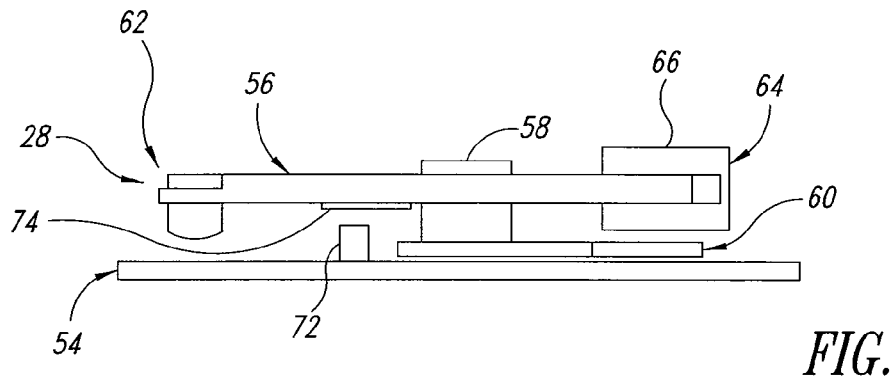
FIGS. 7A-7B schematically illustrate top and side views, respectively, of a first moving mechanism according to the present disclosure.

Referring next to FIG. 7, shown therein is one embodiment of a moving mechanism 28 positioned on a circuit board 54. More particularly, the mechanism 28 has a swing arm 56 rotatably mounted on an axle 58 to rotate thereabout. The axle 58 is fixedly mounted to a base 60 that is attached to the circuit board 54. The arm 56 has a first end 62 adapted to receive the light source and optical system and a second end 64 adapted to receive an electromagnetic device, in this case a voice coil 66.

Figure 7B:
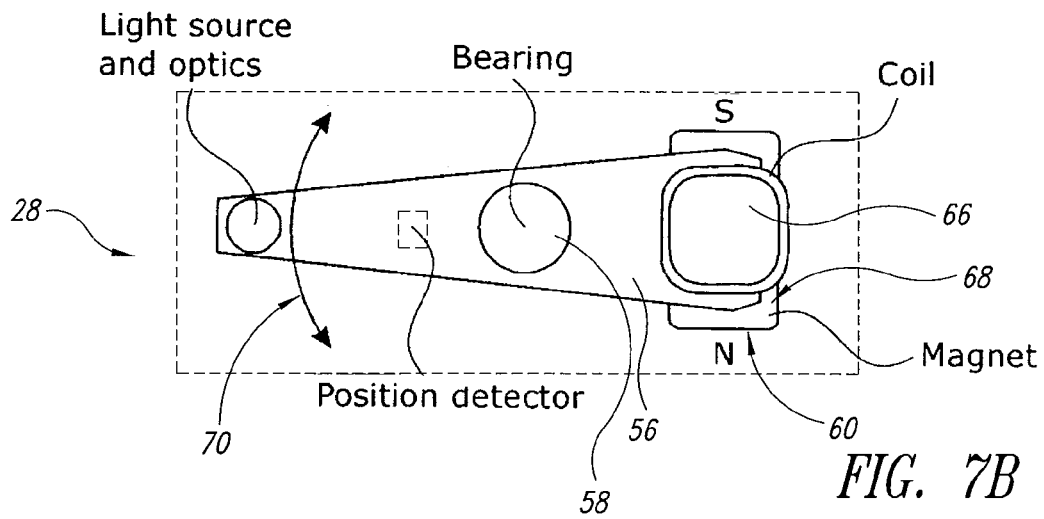

In this embodiment, the base 60 has a magnetized section 68 that cooperates with the voice coil 66 such that when the voice coil is energized by electric current, the electromagnetic field interacts with the magnetized portion 68 to cause the swing arm 56 to rotate about the bearing 58 as shown by the arrows 70 in FIG. 7B. This in turn moves the light source and optics that are to be mounted on the first end 62 of the swing arm 56 in very rapid fashion. A position feedback system can be provided in the form of a position detector 72 mounted on the circuit board 54 that senses the position of one or more magnets 74 positioned on an underside of the swing arm 56 in spaced vertical relationship to the detector 72.

The size of the arm does affect its performance. For example, too long of an arm results in greater weight and slower movement, whereas an arm length that is too short results in an elongation or an enlargement of the treatment area because the arc of movement has a shorter radius. An optimal length is in the range of 20-50 mm from the center of rotation to the light source with an ideal length of 38 mm.

The position detector 72 is preferably a Hall system on the circuit board that detects the magnets 74 on the bottom surface of the arm 56. However, an optical or other known sensing system can be used for position detection.

In use, the controller receives commands from the user for the type of light pattern to be generated, and by signals to the voice coil 66 controls the movement of the arm 56 and hence the pattern of the light beam 30.

In another embodiment, multiple diodes can be mounted on the swing arm 56 that facilitate use of a shorter effective arm length with more light. While this makes the arm effectively heavier and slower, this can be compensated by shortening the length of the arm to approximately 28 mm in length.

The controller 48 can be in the form of a programmable integrated circuit, processor, microprocessor, ASIC, and other known electronic circuits, programmable or non-programmable, that moves the arm 56 in a manner to accomplish the specified or desired treatment.

Figure 8:
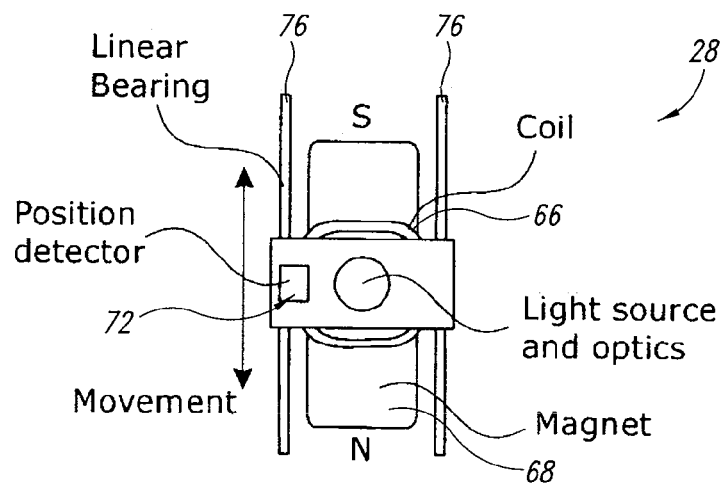
FIG. 8 schematically illustrates a second moving mechanism according to the present disclosure.

FIG. 8 illustrates an alternative embodiment of a movement mechanism 28 in which the coils 66, light source, and optics are mounted for linear movement along rails 76 over a stationary magnet 68. This is another example of a single axis movement mechanism.

FIG. 9 schematically illustrates a moving mechanism for two-dimensional movement of the light source and optical system along the x- and y-axes. This movement would be accomplished by a combination of the foregoing movement mechanisms 28 or with other known two-axis systems.

Various treatment patterns on the target surface are illustrated in FIGS. 10A-10D. In FIG. 10A, the treatment pattern consists of treatment spots 34 having a circular configuration with untreated areas spaced between the treatment spots 34. In FIG. 10B, the treatment spots are very small and not contiguous, leaving large distances between them. FIG. 10C illustrates a staggered pattern of treatment spots, while FIG. 10D illustrates a random pattern of treatment spots 34.

There are unique advantages to each of the example patterns shown in FIGS. 10A-10D. The pattern in FIG. 10A achieves a high coverage of the target surface that is required for some treatments, while the array of spaced-apart spots in 10B reduces bulk heating between spots and decreases healing time. The distance between spots may range from ½ of a spot size and greater. The staggered array of spots in FIG. 10C leads to decreased risk of generating visible lines on the target surface. In FIG. 10D, the array of randomly positioned spots further decreases the risk of generating visible structures on the target surface. Moreover, the random pattern may be utilized as a safety measure. For example, if the handpiece is kept in the same position for several exposures, i.e., for a longer time than it takes the set of light beams to scan the target surface and revert to its original position, the treatment beam will target different spots on the target surface during successive passes across the target surface to reduce the risk of excessive treatment.

In the two left-most treatment patterns shown in FIGS. 11A-11B, the laser light beams are not turned off between the spots. Rather the spots are illuminated with a high fluence while the fluence is decreased between the spots. In this way, tissue between the spots is also stimulated for further enhancement of the post treatment healing effect.

The spots may be treated with continuous light beams while the set of light beams remain in the same position or moves slowly past the spots, and tissue between the spots may be treated with lower fluence, e.g., by faster movement of the set of light beams.

The two right-most patterns of FIGS. 11C-11D illustrate a treatment pattern that is obtained by movement of the set of light beams from spot to spot in several passes, e.g., for example by treating equidistant spots during a first scan across the target area followed by a second scan where the pattern of equidistant spots is offset in relation to the spots of the first pass. This may continue until the entire target area has been treated.

FIGS. 12A-12B show treatment patterns made by a handpiece with a single light source that is moved linearly in one dimension (horizontal in FIGS. 12A-12B) while the handpiece is moved manually in a direction perpendicular to the scanning direction of the light beam. In the left-most treatment pattern in FIG. 12A, the light source is pulsed forming treated spots with untreated tissue between the spots. The lines of spots form slightly skewed lines with respect to the horizontal scanning direction because of the manual movement of the handpiece in the vertical direction of FIG. 12A.

In the right-most treatment pattern of FIG. 12B, the laser emits a continuous light beam forming treatment patterns treated with high fluence light and lines between patterns treated with light of a lower fluence.

The distance between scanned lines in FIGS. 12A-12B will depend on the manual movement of the handpiece 40. In this regard, the handpiece has a position sensor (not shown) for detecting movement of the handpiece, e.g., for detection of moving speed of the handpiece. The position detector may be of a well-known type, e.g., from a computer mouse. A detected movement value, e.g., a speed value, may be displayed on the display 46 shown in FIG. 3 of the handpiece 40 to assist the user of the handpiece 40 in maintaining a desired movement of the handpiece 40 across a tissue surface. A movement sensor may be incorporated in any of the illustrated handpieces.

The positioning of the movable set of light beams in the handpiece has the important advantage that spots illuminated on the target surface can be very small. A spot size of tens of microns using a laser diode can be achieved with a simple optical system.

This small spot size results in a very high power density of many $kW/cm^2$ and a correspondingly high fluence of hundreds or thousands of $J/cm^2$.

The table below shows typical spot sizes, power density and fluence for one embodiment:

|  | Power density | Fluence 10 ms pulse |
|---|---|---|
| 2 W output 30 × 150 µm spot size | 44 $kW/cm^2$ | 440 $J/cm^2$ |
| 5 W output 10 × 500 µm spot size | 100 $kW/cm^2$ | 1000 $J/cm^2$ |
| 1 W output 70 × 70 µm spot size | 20 $kW/cm^2$ | 204 $J/cm^2$ |
| 10 W output 100 × 100 µm spot size | 100 $kW/cm^2$ | 1000 $J/cm^2$ |
| 100 mW output 50 × 500 µm spot size | 400 $W/cm^2$ | 4 $J/cm^2$ |

These power densities and fluences on the target surface are very high and obtained by a low power light source, high enough to cause ablation and achieve an acoustic-optical effect in skin tissue, where the instant heat generates a physical rupture of the skin.

Figure 13:
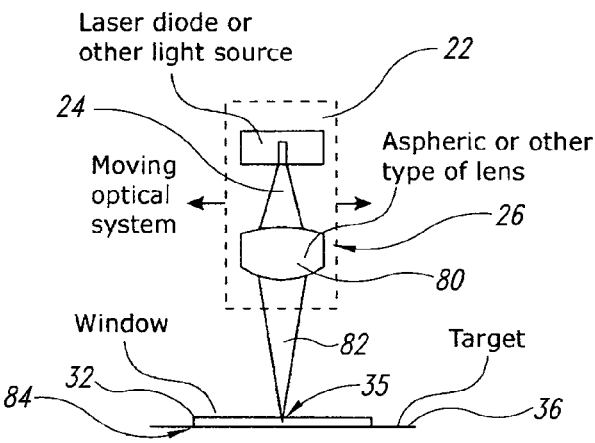
FIG. 13 schematically illustrates an optical system with one light source of an embodiment of the present disclosure.

The optical system may be realized in varied ways. In one embodiment shown in FIG. 13, the optical system 26 includes a single aspheric lens 80 that focuses a single output beam 82 from a single laser diode 22 at the outer surface 84 of the output window 32, i.e., near the target surface 36 when the handpiece is used. Positioning of the focal point 35 of the light beam 82 slightly above the target surface 36 during treatment may reduce the power density in a treated spot. In the illustrated embodiment, the moving mechanism moves both the single light source and the optical system together.

It is preferred to have a simple optical system to keep the moving mass low and to reduce optical losses and complexity. A low moving mass allows faster movement between spot positions.

Figure 14:
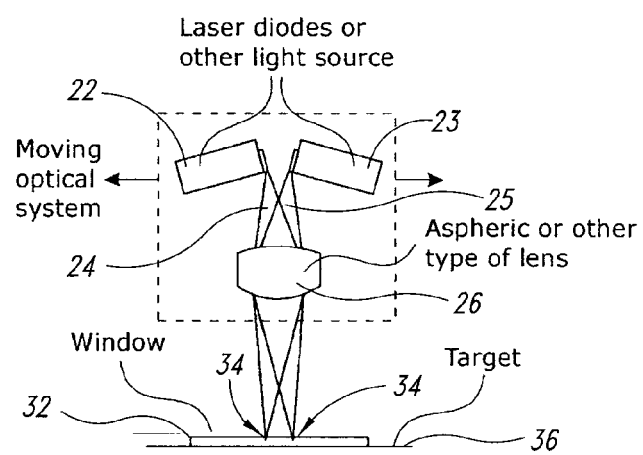
FIG. 14 schematically illustrates an optical system with two light sources of an embodiment of the present disclosure.

As shown in FIG. 14, several spots 34 may be illuminated simultaneously with a similar simple optical system. In the illustrated embodiment, the set of light sources consists of two light sources 22, 23 for simultaneous illumination of two discrete target spots 34 using two emitted lights 24, 25.

Figure 15:
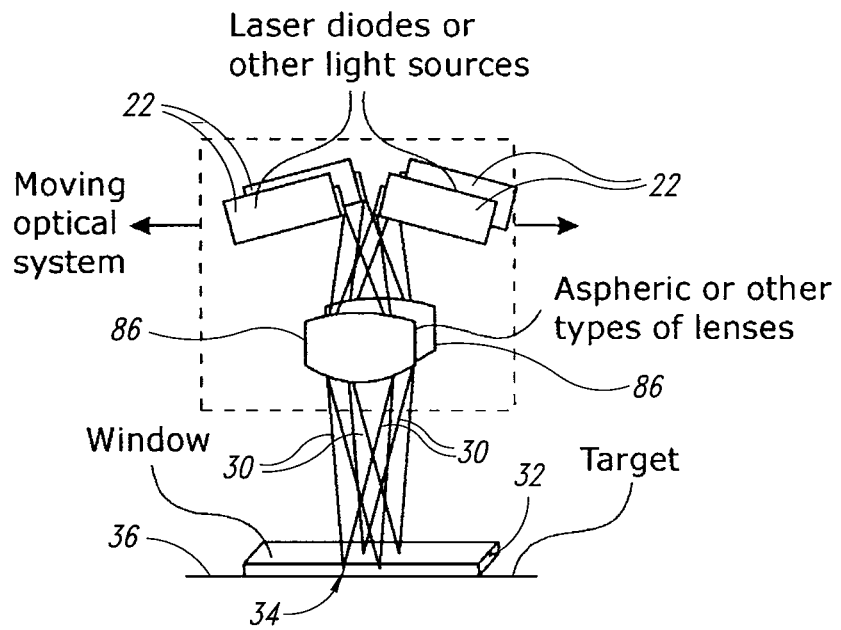
FIG. 15 schematically illustrates an optical system with a plurality of light sources of an embodiment of the present disclosure.

As shown in FIG. 15, several spots 34 may be illuminated simultaneously with a similar optical system. In the illustrated embodiment, the optical system 26 has an array of micro-lenses 86 for focusing the set of light beams 30 from a plurality of light sources 22 onto a plurality of spots 34 on the target surface 36.

Figure 16:
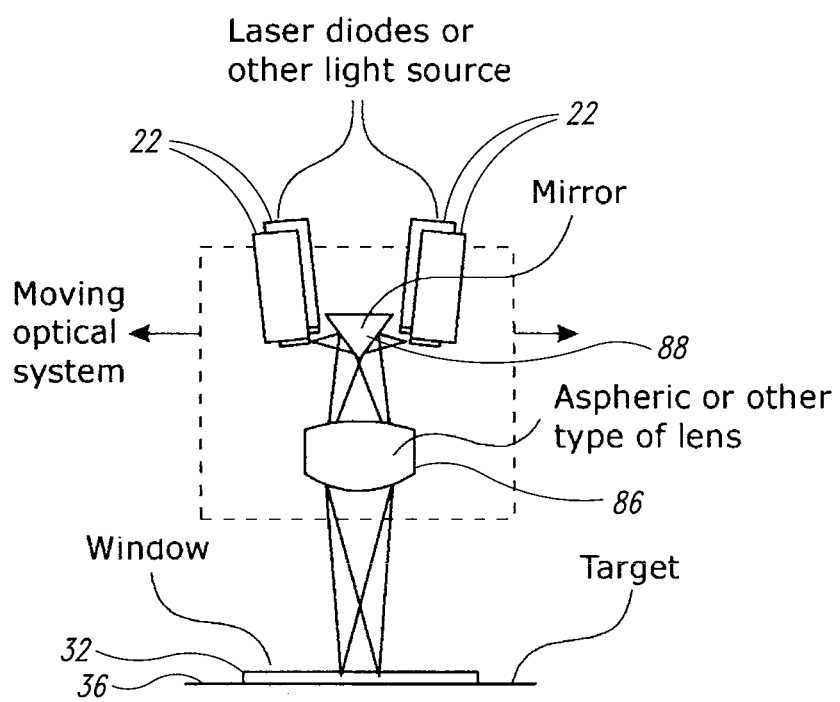
FIG. 16 schematically illustrates yet another optical system of an embodiment of the present disclosure.

In yet another embodiment shown schematically in FIG. 16, the optical system 26 has a single lens and a prismatic mirror 88 for focusing four light beams onto four spots on the target surface. In embodiments with a plurality of light sources 22, the light sources 22 can have different wavelengths and can be switched on and off at different times to achieve a desired treatment.

Figure 17:
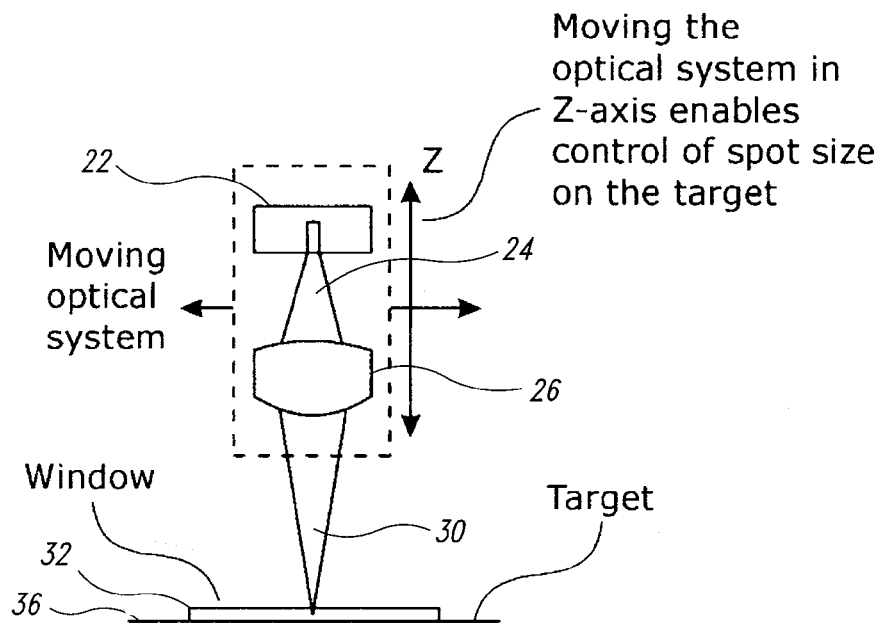
FIG. 17 schematically illustrates a fifth embodiment of the present disclosure.

In the embodiment shown in FIG. 17, the optical system is moved in the direction of the z-axis for controlled adjustment of the distance between the optical system 26 and the target surface 36 whereby the size of the illuminated spots 34 on the target surface may be adjusted.

In one embodiment, the movement mechanism is adapted to move the treatment spot in one dimension, and the handpiece 40 is moved across the skin by the operator to form a two-dimensional treatment area.

Figure 18:
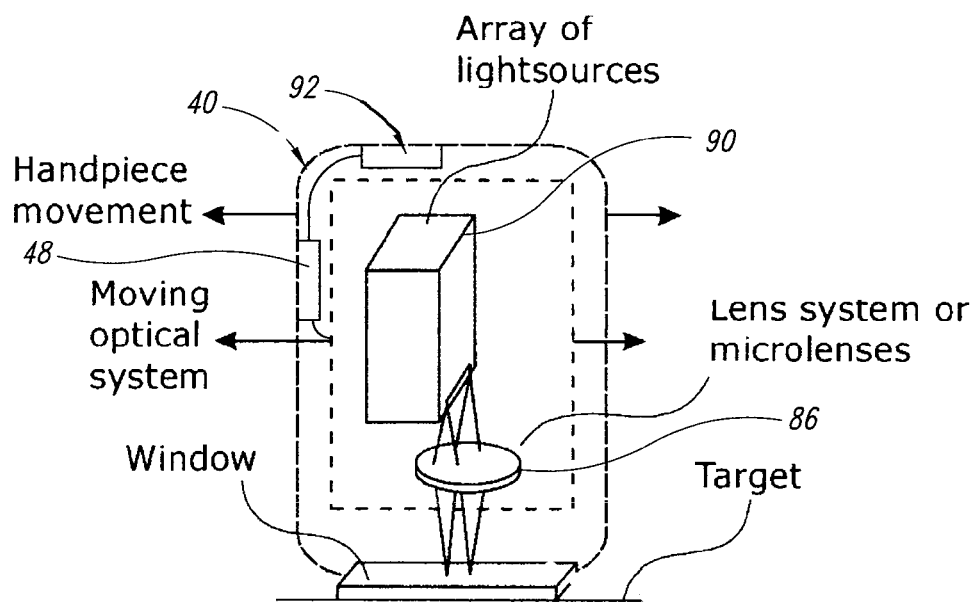
FIG. 18 schematically illustrates a sixth embodiment of the present disclosure.

In another embodiment shown in FIG. 18, an array of light sources 90 is moved inside the handpiece 40 to counteract possible involuntary movement of the handpiece for illumination of non-moving spots on the target surface. The illustrated embodiment comprises a movement detector 92 for detection of the involuntary or voluntary movements of the handpiece 40. The controller 48 is adapted to control the moving mechanism 28 to move the set of light sources 90 in the opposite direction of the involuntary movements and at the same speed. This results in a constant speed of the light beam 30 application to the target surface 36 during movement of the handpiece 40, including unsteady or uneven movement as well as steady but too slow or too fast handpiece movement.

When the moving mechanism 28 reaches an end point, the controller turns the light sources 90 off and directs the movement mechanism 28 to fast forward to the other end of the movement range. The procedure is then repeated. The moving mechanism 28 counteracting involuntary movements of the handpiece 40 is used to illuminate stationary spots on the target surface 36 with high power density and fluence values.

Figure 19:
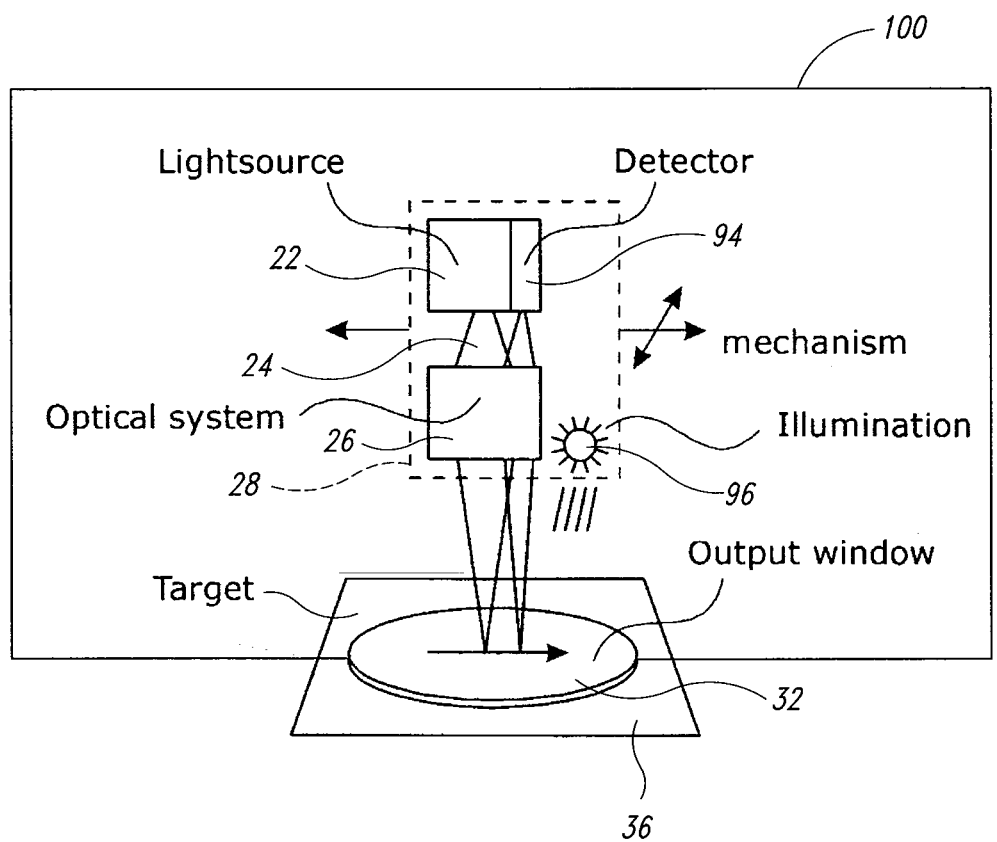
FIG. 19 schematically illustrates a seventh embodiment of the present disclosure.

The handpiece 100 shown in FIG. 19 further includes a sensor 94 for detection of a parameter of the target surface 36. The controller 48 can modify the treatment in response to the detected parameter values. In this way, the treatment may be automatically optimized to various types of tissue surfaces. This may reduce treatment time and may reduce possible discomfort, e.g., pain. A source of illumination 96 is also provided to enhance visual inspection of the target surface 36.

For example, dark areas and light areas (e.g., hypo- or hyper-pigmentation) are automatically treated differently, and areas that do not need treatment are automatically not treated. Likewise, wrinkles are treated automatically while areas without wrinkles are not treated, and vascular defects or acne are treated automatically while areas without defects are not treated, and so forth.

The detector can be adapted to sense an area ahead of the treatment beam and sense one or more parameters of light reflected from the area. The controller adjusts the treatment by adjusting the light beam parameters in response to the sensed parameters and controls the set of light sources 22 and the moving mechanism 28 accordingly when the set of light beams reaches the respective area.

In another embodiment, the detector 94 is positioned in such a way that it senses the reflected light from the treatment beam and the controller 48 is adapted to control the set of light sources 22 and the moving mechanism 28 in response thereto.

The handpiece 100 illustrated in FIG. 19 may be used in accordance with the following procedure:

First the handpiece is placed on an area of a skin surface having at least one area that should not receive treatment and one area that should receive treatment. A sample button on the handpiece housing is pressed, and the handpiece scans the area with the detector 94 and determines parameters used during treatment of subsequent areas. The determined parameters are stored in a memory in the handpiece.

Subsequently, the handpiece 100 is placed on other areas and a start button on the handpiece housing is pressed. The controller 48 then automatically determines how to treat various types of tissue surface within the area covered by the handpiece based on the stored parameters obtained during the initial sample scan and treats the area accordingly.

The handpiece 100 in another embodiment includes an energy meter (not shown) for monitoring the amount of optical energy delivered to a surface during treatment. The energy meter includes an energy counter for counting the amount of energy delivered by the handpiece during treatment. The count value may be displayed to the user on the display in the handpiece housing. In this way, the user will be able to control the amount of energy delivered to the treated surface. When the user starts the treatment, the energy counter is set to 0. During treatment, the counter sums up the total energy emitted by the set of light sources. An energy threshold may be set by the user and stored in a memory in the handpiece 100. The handpiece 100 may be adapted to indicate to the user when the energy threshold has been reached and upon such indication, the user may decide to stop treatment.

The display 46 may show the amount of delivered energy as a percentage of the energy threshold so that the user gain knowledge on to which extent the desired treatment has already been performed and optionally the amount of time, energy, etc., left for the area.

The energy meter determines the amount of delivered energy independent of possible pauses in the treatment and accurately determines treatment progress. The determination is also independent of handpiece movement and the type of scanning e.g., one-dimensional scanning or two-dimensional scanning. It will provide a highly repeatable treatment regime for the area in question.

The handpiece 100 in another embodiment includes a user interface that utilizes a start treatment button, means for selection of treatment area, such as a forehead, a chin, a cheek, a hand or other body parts, means for energy selection, and means for fluence selection.

The display 46 in the handpiece 100 may show various parameters and may show an image of the skin being treated to assist the operator in selection of tissue areas for treatment. The display may display many other parameters, such as: treatment progress, fluence, power density, energy settings, and battery status.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A handpiece for treatment of a target tissue surface with at least one light beam, the handpiece comprising:
   a housing;
   at least one light source for generating at least one light beam, the at least one light source located in the housing of the handpiece;
   an opening for allowing emission of the at least one light beam out of the housing and towards the target tissue surface;
   a mechanism for controlled displacement of the at least one light source relative to the housing; and
   a controller for controlling the mechanism, the controller being an electronic controller, wherein the controller is configured to control the mechanism and the at least one light source to provide a treatment pattern comprising individual treatment spots on the target tissue surface.

2. The handpiece according to claim 1, further comprising an optical system for focusing the at least one light beam.

3. The handpiece according to claim 1, wherein the at least one light source comprises a laser diode.

4. The handpiece according to claim 1, wherein the at least one light source comprises a light emitting diode.

5. The handpiece according to claim 1, wherein the mechanism is adapted for one-dimensional displacement of the at least one light source.

6. The handpiece according to claim 1, wherein the mechanism is adapted for two-dimensional displacement of the at least one light source.

7. The handpiece according to claim 1, wherein the mechanism is adapted for three-dimensional displacement of the at least one light source.

8. The handpiece according to claim 1, further comprising:
   an output port for emission of the at least one light beam; and
   an optical system;
   wherein the output port has a window that is configured to be in contact with the target tissue surface during treatment, and wherein the optical system is adapted to focus the at least one light beam at an outer surface of the window.

9. The handpiece according to claim 1, wherein the light source is adapted to deliver more than 50 $J/cm^2$.

10. The handpiece according to claim 1, wherein the controller is adapted to control the mechanism such that the treatment spots are arranged in an array of rows and columns on the target tissue surface.

11. The handpiece according to claim 1, wherein the controller is adapted to control the mechanism such that the treatment spots are arranged in an array of staggered rows on the target tissue surface.

12. The handpiece according to claim 1, wherein the controller is adapted to control the mechanism such that the treatment spots are arranged randomly on the target tissue surface.

13. The handpiece according to claim 2, wherein the mechanism is further adapted to displace the optical system together with the at least one light source.

14. The handpiece according to claim 2, wherein the optical system comprises at least one lens.

15. The handpiece according to claim 2, wherein the optical system comprises an array of micro-lenses.

16. The handpiece according to claim 2, wherein the optical system comprises a diffractive optical element.

17. The handpiece according to claim 1, wherein the housing further accommodates a detector for detection of light emanating from the target tissue surface, the detector connected to the controller, and wherein the controller is further adapted for determination of a tissue parameter based on an output from the detector.

18. The handpiece according to claim 17, wherein the detector is positioned for detection of light emanating from the target tissue surface in front of the at least one light beam, and wherein the controller is further adapted for modifying illumination of the target tissue surface in response to the determined tissue parameter.

19. The handpiece according to claim 2, wherein the at least one light beam comprises a set of light beams, and wherein the optical system is adapted to focus the set of light beams to a set of elongated spots, each spot having a smallest width smaller than 20 μm and a largest width smaller than 200 μm.

20. The handpiece of claim 1, further comprising an optical system for focusing the at least one light beam to a spot having a minimum width less than 50 μm.

21. The handpiece according to claim 20, wherein the spot is elongated with a ratio between length and width that is larger than 5:1.

22. The handpiece according to claim 20, adapted for illuminating the spot on the tissue surface with a fluence of more than 150 J/cm$^2$.

23. The handpiece according to claim 20, adapted for illuminating the spot on the tissue surface with a power density of more than 10 kW/cm$^2$.

24. A method for treating a target surface of a tissue with a light beam, comprising:
   directing a light beam from a light source in a handpiece towards the target surface;
   focusing the light beam at the target surface so that a focal point is positioned proximate the target surface so that a diameter of the light beam is smaller at the target surface than below the target surface of the tissue; and
   moving the light source in the handpiece relative to a housing of the handpiece and controlling an activation of the light source using an electronic controller to provide a treatment pattern comprising individual treatment spots on the target surface.

25. The method according to claim 24, further comprising focusing the light beam such that an area illuminated on the target surface of the tissue by the light beam is less than 0.2 mm$^2$.

26. The method according to claim 24, further comprising focusing the light beam such that an illuminated spot resulted by the light beam on the target surface of tissue receives a power density of more than 10 kW/cm$^2$ for ablation of a small tissue area, resulting in increased transparency through an upper part of the tissue and thereby allowing treatment of deeper tissue structures.

27. A method for treating human skin, comprising:
   using a light beam with a wavelength of between 400 nm and 4000 nm and a power density sufficiently high for temporarily creating a tunnel into the skin resulting in increased transparency through the skin and thereby allowing treatment of deeper tissue structures, wherein the light beam is generated from a light source in a handpiece; and
   moving the light source in the handpiece relative to a housing of the handpiece and controlling an activation of the light source to provide a treatment pattern comprising individual treatment spots on the skin.

28. The method according to claim 27, further comprising applying a treating substance to a treatment area before optical treatment, the optical treatment resulting in increased penetration through the skin to the previously applied substance.

29. The method according to claim 27, further comprising focusing the light beam such that an area illuminated on the skin is less than 0.2 mm$^2$ and receives a power density sufficiently high for creating a tunnel into the skin resulting in increased penetration through the skin of a substance.

30. A method for treating human skin with a light beam comprising:
   generating the light beam using a light source in a handpiece;
   focusing the light beam on treatment spots on the skin, the treatment spots having an area at a surface of the skin sufficiently small to cause the treatment spots not to be visible to a naked eye at a viewing distance of 30 cm or more; and
   moving the light source in the handpiece relative to a housing of the handpiece and controlling an activation of the light source using an electronic controller to provide a treatment pattern comprising individual treatment spots on the skin.

31. A method for treating human skin with a light beam, comprising:
   generating a light beam using a light source in a handpiece;
   irradiating a surface of the skin with a spot illuminated by the light beam, the spot having an area smaller than 0.1 mm$^2$ thereby causing the irradiated surface area to heal very quickly; and
   moving the light source in the handpiece relative to a housing of the handpiece and controlling an activation of the light source using an electronic controller to provide a treatment pattern comprising individual treatment spots on the target tissue surface.

32. A method for treating a target tissue surface on a human skin with a light beam, comprising:
   generating the light beam using a light source in a handpiece;
   focusing the light beam such that an area of a spot illuminated on the target tissue surface is less than 0.5 mm$^2$ and receives a power density sufficiently high for creating a tunnel into the skin thereby enhancing an effect of a substance applied to the target tissue surface; and
   moving the light source in the handpiece relative to a housing of the handpiece.

33. The method according to claim 32, wherein the area of the spot illuminated on the target tissue surface is less than 0.4 mm$^2$.

34. The method according to claim 33, wherein the area of the spot illuminated on the target tissue surface is less than 0.3 mm$^2$.

35. The method according to claim 34, wherein the area of the spot illuminated on the target tissue surface is less than 0.2 mm$^2$.

36. The method according to claim 35, wherein the area of the spot illuminated on the target tissue surface is less than 0.1 mm$^2$.

37. The method of claim 32, further comprising controlling an activation of the light source, wherein the act of moving and the act of controlling are performed to provide a treatment pattern comprising individual treatment spots on the target tissue surface.

38. A handpiece for treatment of a target tissue surface with at least one light beam, the handpiece comprising:
- a housing;
- at least one light source for generating at least one light beam, the at least one light source located in the housing of the handpiece;
- an opening for allowing emission of the at least one light beam out of the housing and towards the target tissue surface;
- a mechanism for controlled displacement of the at least one light source relative to the housing; and
- a controller for controlling the mechanism, wherein the controller is configured to control the mechanism and the at least one light source to provide a treatment pattern comprising individual treatment spots on the target tissue surface;
- wherein the mechanism comprises an electromagnetic field source for providing an electromagnetic field to move the at least one light source relative to the housing, and wherein the at least one light source is mounted on a swing arm to allow the at least one light source to move relative to the housing in an arc path.

39. The handpiece of claim 38, wherein the at least one light source comprises a first light source and a second light source.

40. The handpiece of claim 38, wherein the electromagnetic field source comprises a coil.

41. The handpiece of claim 38, further comprising an optical system for focusing the at least one light beam.

42. The handpiece of claim 38, wherein the at least one light source comprises a laser diode.

43. The handpiece of claim 38, wherein the at least one light source comprises a light emitting diode.

44. The handpiece of claim 38, wherein the controller is configured to control the mechanism such that the treatment spots are arranged in an array of rows and columns on the target tissue surface.

45. The handpiece of claim 38, wherein the controller is configured to control the mechanism such that the treatment spots are arranged in an array of staggered rows on the target tissue surface.

46. The handpiece of claim 38, wherein the controller is configured to control the mechanism such that the treatment spots are arranged randomly on the target tissue surface.

47. A handpiece for treatment of a target tissue surface, comprising:
- a housing;
- a support in the housing, wherein the support is moveable relative to the housing;
- at least one light source mounted to the support for generating at least one light beam, the at least one light source located in the housing of the handpiece; and
- a movement mechanism for displacement of the at least one light source relative to the housing, wherein the movement mechanism comprises an electromagnetic field source for providing an electromagnetic field to move the support relative to the housing.

48. The handpiece of claim 47, wherein the at least one light source comprises a first light source and a second light source.

49. A handpiece for treatment of a target tissue surface, comprising:
- a housing;
- a support in the housing, wherein the support is moveable relative to the housing;
- at least one light source mounted to the support for generating at least one light beam, the at least one light source located in the housing of the handpiece; and
- a movement mechanism for displacement of the at least one light source relative to the housing, wherein the movement mechanism comprises an electromagnetic field source for providing an electromagnetic field to move the support relative to the housing;
- wherein the support to which the at least one light source is mounted is moveable relative to the housing in an arc path.

50. The handpiece of claim 49, wherein the support comprises a swing arm, the one or more light source is located at a first end of the swing arm, and a part of the movement mechanism is located at a second end of the swing arm, the second end being opposite from the first end.

51. The handpiece of claim 49, wherein the electromagnetic field source comprises a coil.

52. The handpiece of claim 49, further comprising an optical system for focusing the at least one light beam.

53. The handpiece of claim 49, wherein the at least one light source comprises a laser diode.

54. The handpiece of claim 49, wherein the at least one light source comprises a light emitting diode.

55. The handpiece of claim 49, further comprising a controller configured to control the mechanism and the at least one light source to provide a treatment pattern having treatment spots arranged in an array of rows and columns on the target tissue surface.

56. The handpiece of claim 49, further comprising a controller configured to control the mechanism and the at least one light source to provide a treatment pattern having treatment spots arranged in an array of staggered rows on the target tissue surface.

57. The handpiece of claim 49, further comprising a controller configured to control the mechanism and the at least one light source to provide a treatment pattern having treatment spots arranged randomly on the target tissue surface.

58. The handpiece of claim 49, wherein the at least one light source comprises a first light source and a second light source.

59. A handpiece for treatment of a target tissue surface, comprising:
- a housing;
- a support in the housing, wherein the support is moveable relative to the housing;
- at least one light source mounted to the support for generating at least one light beam, the at least one light source located in the housing of the handpiece;
- a movement mechanism for displacement of the at least one light source relative to the housing, wherein the movement mechanism comprises an electromagnetic field source for providing an electromagnetic field to move the support relative to the housing; and
- one or more rails, and wherein the support to which the at least one light source is mounted is moveably coupled to the one or more rails so that the support is translatable relative to the one or more rails in a rectilinear path.

60. The handpiece of claim 59, wherein the electromagnetic field source comprises a coil.

61. The handpiece of claim 59, further comprising an optical system for focusing the at least one light beam.

62. The handpiece of claim 59, wherein the at least one light source comprises a laser diode.

63. The handpiece of claim 59, wherein the at least one light source comprises a light emitting diode.

64. The handpiece of claim 59, further comprising a controller configured to control the mechanism and the at least one light source to provide a treatment pattern having treatment spots arranged in an array of rows and columns on the target tissue surface.

65. The handpiece of claim 59, further comprising a controller configured to control the mechanism and the at least one light source to provide a treatment pattern having treatment spots arranged in an array of staggered rows on the target tissue surface.

66. The handpiece of claim 59, further comprising a controller configured to control the mechanism and the at least one light source to provide a treatment pattern having treatment spots arranged randomly on the target tissue surface.

67. The handpiece of claim 59, wherein the at least one light source comprises a first light source and a second light source.

68. A handpiece for treatment of a target tissue surface, comprising:
- a housing;
- a support in the housing, wherein the support is moveable relative to the housing;
- at least one light source mounted to the support for generating at least one light beam, the at least one light source located in the housing of the handpiece; and
- a movement mechanism for displacement of the at least one light source relative to the housing, wherein the movement mechanism comprises an electromagnetic field source for providing an electromagnetic field to move the support relative to the housing;
- wherein the movement mechanism further comprises a magnetic component for interacting with the electromagnetic field source magnetically.

69. The handpiece of claim 68, wherein the electromagnetic field source comprises a coil.

70. The handpiece of claim 68, further comprising an optical system for focusing the at least one light beam.

71. The handpiece of claim 68, wherein the at least one light source comprises a laser diode.

72. The handpiece of claim 68, wherein the at least one light source comprises a light emitting diode.

73. The handpiece of claim 68, further comprising a controller configured to control the mechanism and the at least one light source to provide a treatment pattern having treatment spots arranged in an array of rows and columns on the target tissue surface.

74. The handpiece of claim 68, further comprising a controller configured to control the mechanism and the at least one light source to provide a treatment pattern having treatment spots arranged in an array of staggered rows on the target tissue surface.

75. The handpiece of claim 68, further comprising a controller configured to control the mechanism and the at least one light source to provide a treatment pattern having treatment spots arranged randomly on the target tissue surface.

76. The handpiece of claim 68, wherein the at least one light source comprises a first light source and a second light source.

* * * * *